US009572866B2

(12) United States Patent
Vale, Jr. et al.

(10) Patent No.: US 9,572,866 B2
(45) Date of Patent: Feb. 21, 2017

(54) UROCORTIN 2 ANALOGS AND USES THEREOF

(71) Applicants: Research Development Foundation, Carson City, NV (US); Research Development Foundation, Carson City, NV (US)

(72) Inventors: Wylie W. Vale, Jr.; Joan M. Vaughan, San Diego, CA (US); Cindy Donaldson, San Diego, CA (US); Wolfgang Fischer, Encinitas, CA (US); Jean E. F. Rivier, La Jolla, CA (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 14/802,812

(22) Filed: Jul. 17, 2015

(65) Prior Publication Data

US 2015/0315257 A1  Nov. 5, 2015

Related U.S. Application Data

(62) Division of application No. 13/392,828, filed as application No. PCT/US2010/046890 on Aug. 27, 2010, now abandoned.

(60) Provisional application No. 61/237,995, filed on Aug. 28, 2009.

(51) Int. Cl.
 *C07K 14/47* (2006.01)
 *A61K 38/22* (2006.01)
 *C07K 14/575* (2006.01)

(52) U.S. Cl.
 CPC ....... *A61K 38/2228* (2013.01); *C07K 14/4705* (2013.01); *C07K 14/57509* (2013.01); *Y10T 428/13* (2015.01)

(58) Field of Classification Search
 None
 See application file for complete search history.

(56) References Cited

U.S. PATENT DOCUMENTS

| | | | |
|---|---|---|---|
| 6,214,797 B1 | 4/2001 | Vale, Jr. et al. | |
| 6,353,152 B1 | 3/2002 | Lee et al. | |
| 6,838,274 B2 | 1/2005 | Vale, Jr. et al. | |
| 7,141,546 B1 | 11/2006 | Rivier et al. | |
| 7,223,846 B2 | 5/2007 | Vale, Jr. et al. | |
| 7,459,427 B2 | 12/2008 | Vale, Jr. et al. | |
| 7,488,865 B2 | 2/2009 | Lee et al. | |
| 7,507,794 B2 | 3/2009 | Chen et al. | |
| 2002/0127221 A1* | 9/2002 | Vale, Jr. ............. | C07K 14/57509 424/94.63 |
| 2003/0032587 A1 | 2/2003 | Vale, Jr. et al. | |
| 2005/0191650 A1 | 9/2005 | Vale, Jr. et al. | |
| 2007/0042954 A1 | 2/2007 | Chen et al. | |
| 2007/0191592 A1 | 8/2007 | Vale, Jr. et al. | |
| 2008/0161235 A1 | 7/2008 | Chen et al. | |

FOREIGN PATENT DOCUMENTS

WO   WO 2008/047241   4/2008

OTHER PUBLICATIONS

Isfort et al. Peptides. 27 (2006) 1806-1813.*
Ehrengruber et al. Mol Cel Neuroscience. 17, 855-871 (2001).*
"Neurocrine Biosciences announces initiation of phase I trial with urocortin 2 for congestive heart failure," *Press Release—Neurocrine Biosciences, Inc.*, 2004.
"Neurocrine Biosciences announces urocortin 2 phase II study results in patients with acute decompensated heart failure," *Press Release—Neurocrine Biosciences, Inc.*, 2012.
"Overcoming peptide problems by design," Technical Note PT2-009-1, *Peptides and Immunology*, Mimotopes, pp. 1-3, 2009.
"Primary structure," retrieved from http://en.wikipedia.org/wiki/Primary_structure, retrieved on Mar. 18, 2009.
"UniProtKB/Swiss-Prot. Q99ML8 (UNC2_MOUSE)," retrieved from http://www.uniprot.org/uniprot/Q99ML8, last modified Jul. 9, 2014.
Baram, et al., "The CRF1 receptor mediates the excitatory actions of corticotropin releasing factor (CRF) in the developing rat brain: in vivo evidence using a novel, selective, non-peptide CRF receptor antagonist," *Brain Res.*, 770:89-95, 1997.
Campbell et al., "A protein's shape depends on four levels of structure," Unit 1, The Life of the Cell, *Biology Concepts & Connections*, 5th Edition, 2006.
Cervini, et al., "Corticotropin releasing factor (CRF) agonists with reduced amide bonds and Ser7 substitutions," *J. Med. Chem.*, 42:761-8, 1999.
Chan et al. "Urocortin-2 infusion in acute decompensated heart failure—Findings from the UNICORN study (Urocortin-2 in the treatment of acute heart failure as an adjunct over conventional therapy," *JACC: Heart Failure*, 1(5):433-441, 2013.
Chen et al., "Urocortin 2 modulates glucose utilization and insulin sensitivity in skeletal muscle," *PNAS*, 103(44):16580-16585, 2006.
Chen, et al., "Urocortin II gene is highly expressed in mouse skin and skeletal muscle tissues: localization, basal expression in corticotropin-releasing factor receptor (CRFR) 1- and CRFR2-null mice, and regulation by glucocorticoids," *Endocrinology*, 145:2445-57, 2004.
Fekete and Zorrilla, "Physiology, pharmacology, and therapeutic relevance of urocortins in mammals: ancient CRF paralogs," Front. Neuroendocrinol., 28:1-27, 2008.

(Continued)

*Primary Examiner* — Amber D Steele
*Assistant Examiner* — Schuyler Milton
(74) *Attorney, Agent, or Firm* — Parker Highlander PLLC

(57) ABSTRACT

Disclosed are polypeptides that are analogs of urocortin 2 that have pharmacological activity similar to urocortin 2 but have improved water solubility compared to urocortin 2, and pharmaceutical compositions of the polypeptides of the present invention. Also disclosed are polynucleotides encoding the polypeptides, and methods of treating pathophysiological states employing pharmaceutical compositions of the polypeptides and polynucleotides of the present invention. In addition, disclosed are vectors and host cells that include a nucleic acid encoding a polypeptide of the present invention, and kits that include pharmaceutical compositions of the present invention.

19 Claims, No Drawings

(56) References Cited

OTHER PUBLICATIONS

Fekete, et al., "Systemic urocortin 2, but not urocortin 1 or stressin 1-A, suppresses feeding via CRF2 receptors without malaise and stress," *Br. J. Pharmacol.*, 164:1959-75, 2011.

Fulop et al., "Beta-amyloid-derived pentapeptide RIIGLa inhibits ABeta(1-42) aggregation and toxicity," *Biochem Biophys Res.Com.*, 324:64-69, 2004.

Grace, et al., "Common and divergent structural features of a series of corticotropin releasing factor-related peptides," *J. Am. Chem. Soc.*, 129:16102-14, 2007.

Hsu and Hsueh, "Human stresscopin and stresscopin-related peptide are selective ligands for the type 2 corticotropin-releasing hormone receptor," *Nat. Med.*, 7:605-11, 2001.

Isfort et al., "Modifications of the human urocortin 2 peptide that improve pharmacological properties," *Peptides*, 27:1806-1813, 2006.

Lawrence and Latchman, "The Urocortins: mechanisms of cardioprotection and therapeutic potential," *Mini Rev. Med. Chem.*, 6:1119-26, 2006.

Martinez and Taché, "CRF1 receptors as a therapeutic target for irritable bowel syndrome," *Curr. Pharm. Des.*, 12:4071-88, 2006.

Meili-Butz, et al., "Acute effects of urocortin 2 on cardiac function and propensity for arrhythmias in an animal model of hypertension-induced left ventricular hypertrophy and heart failure," *Eur. J. Heart Fail.*, 12:797-804, 2010.

Office Action issued in European Application No. 10749982.4, mailed Apr. 3, 2014.

Office Action issued in U.S. Appl. No. 13/392,828, mailed Aug. 28, 2012.

Office Action issued in U.S. Appl. No. 13/392,828, mailed Aug. 1, 2014.

Office Action issued in U.S. Appl. No. 13/392,828, mailed Aug. 15, 2013.

Office Action issued in U.S. Appl. No. 13/392,828, mailed Dec. 12, 2012.

Office Action issued in U.S. Appl. No. 13/392,828, mailed May 18, 2015.

Pan and Kastin, "Urocortin and the brain," *Prog. Neurobiol.*, 84:148-56, 2008.

PCT International Search Report and Written Opinion, issued in Application No. PCT/US2010/046890, dated Feb. 3, 2011.

PCT Partial Search Report, issued in Application No. PCT/US2010/046890, dated Nov. 18, 2010.

Rademaker, et al., "Prolonged urocortin 2 administration in experimental heart failure: sustained hemodynamic, endocrine, and renal effects," *Hypertension*, 57:1136-44, 2011.

Reutenauer-Patte, et al., "Urocortins improve dystrophic skeletal muscle structure and function through both PKA- and Epac-dependent pathways," *Am. J. Pathol.*, 180:749-62, 2012.

Reyes, et al., "Urocortin II: a member of the corticotropin-releasing factor (CRF) neuropeptide family that is selectively bound by type 2 CRF receptors," *Proc. Natl. Acad. Sci. USA*, 98:2843-8, 2001.

Smani, et al., "Urocortin-2 induces vasorelaxation of coronary arteries isolated from patients with heart failure," *Clin. Exp. Pharmacol. Physiol.*, 38:71-6, 2011.

Spencer and Verma, "Targeted delivery of proteins across the blood-brain barrier," *Proc. Natl. Acad. Sci. USA*, 104:7594-9, 2007.

Tao, et al., "Activation of corticotropin-releasing factor receptor 1 selectively inhibits CaV3.2 T-type calcium channels," *Mol. Pharmacol.*, 73:1596-609, 2008.

Xiao et al., "Increasing solubility of proteins and peptides by site-specific modification with betaine," *Bioconjug Chem*, 19(6):1113-1118, 2008.

\* cited by examiner

SEQUENCE LISTING

```
<160> NUMBER OF SEQ ID NOS: 22

<210> SEQ ID NO 1
<211> LENGTH: 38
<212> TYPE: PRT
<213> ORGANISM: Artificial Sequence
<220> FEATURE:
<223> OTHER INFORMATION: Synthetic peptide

<400> SEQUENCE: 1

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val
        35

<210> SEQ ID NO 2
<211> LENGTH: 39
<212> TYPE: PRT
<213> ORGANISM: Artificial Sequence
<220> FEATURE:
<223> OTHER INFORMATION: Synthetic peptide

<400> SEQUENCE: 2

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val Gly
        35
```

<210> SEQ ID NO 3
<211> LENGTH: 40
<212> TYPE: PRT
<213> ORGANISM: Artificial Sequence
<220> FEATURE:
<223> OTHER INFORMATION: Synthetic peptide

<400> SEQUENCE: 3

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val Gly His
        35                  40

<210> SEQ ID NO 4
<211> LENGTH: 41
<212> TYPE: PRT
<213> ORGANISM: Artificial Sequence
<220> FEATURE:
<223> OTHER INFORMATION: Synthetic peptide

<400> SEQUENCE: 4

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val Gly His Cys
        35                  40

<210> SEQ ID NO 5
<211> LENGTH: 38
<212> TYPE: PRT
<213> ORGANISM: Artificial Sequence
<220> FEATURE:
<223> OTHER INFORMATION: Synthetic peptide

<400> SEQUENCE: 5

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val
        35

<210> SEQ ID NO 6
<211> LENGTH: 39
<212> TYPE: PRT
<213> ORGANISM: Artificial Sequence
<220> FEATURE:
<223> OTHER INFORMATION: Synthetic peptide

<400> SEQUENCE: 6

Arg Ile Val Leu Ser Leu Asp Val Pro Ile Gly Leu Leu Gln Ile Leu
1               5                   10                  15

Leu Glu Gln Ala Arg Ala Arg Ala Ala Arg Glu Gln Ala Thr Thr Asn
            20                  25                  30

Ala Arg Ile Leu Ala Arg Val
        35

<210> SEQ ID NO 7

<211> LENGTH: 43
<212> TYPE: PRT
<213> ORGANISM: Artificial Sequence
<220> FEATURE:
<223> OTHER INFORMATION: Synthetic peptide

<400> SEQUENCE: 7

```
His Pro Gly Ser Arg Ile Val Leu Ser Leu Asp Val Pro Ile Gly Leu
1               5                   10                  15

Leu Gln Ile Leu Leu Glu Gln Ala Arg Ala Arg Ala Arg Glu Gln
            20                  25                  30

Ala Thr Thr Asn Ala Arg Ile Leu Ala Arg Val
        35                  40
```

<210> SEQ ID NO 8
<211> LENGTH: 51
<212> TYPE: PRT
<213> ORGANISM: Artificial Sequence
<220> FEATURE:
<223> OTHER INFORMATION: Synthetic peptide

<400> SEQUENCE: 8

```
Cys Ser Pro Thr Arg His Pro Gly Ser Arg Ile Val Leu Ser Leu Asp
1               5                   10                  15

Val Pro Ile Gly Leu Leu Gln Ile Leu Leu Glu Gln Ala Arg Ala Arg
            20                  25                  30

Ala Ala Arg Glu Gln Ala Thr Thr Asn Ala Arg Ile Leu Ala Arg Val
        35                  40                  45

Gly His Cys
    50
```

<210> SEQ ID NO 9
<211> LENGTH: 85
<212> TYPE: PRT
<213> ORGANISM: Artificial Sequence
<220> FEATURE:
<223> OTHER INFORMATION: Synthetic peptide

<400> SEQUENCE: 9

```
Ile Pro Thr Phe Gln Leu Arg Pro Gln Asn Ser Pro Gln Thr Thr Pro
1               5                   10                  15

Arg Pro Ala Ala Ser Glu Ser Pro Ser Ala Ala Pro Thr Trp Pro Trp
            20                  25                  30

Ala Ala Gln Ser His Cys Ser Pro Thr Arg His Pro Gly Ser Arg Ile
        35                  40                  45

Val Leu Ser Leu Asp Val Pro Ile Gly Leu Leu Gln Ile Leu Leu Glu
    50                  55                  60

Gln Ala Arg Ala Arg Ala Ala Arg Glu Gln Ala Thr Thr Asn Ala Arg
65                  70                  75                  80

Ile Leu Ala Arg Val
            85
```

<210> SEQ ID NO 10
<211> LENGTH: 38
<212> TYPE: PRT
<213> ORGANISM: Artificial Sequence
<220> FEATURE:
<223> OTHER INFORMATION: Synthetic peptide

<400> SEQUENCE: 10

```
Val Ile Leu Ser Leu Asp Val Pro Ile Gly Leu Leu Arg Ile Leu Leu
1               5                   10                  15
```

Glu Gln Ala Arg Tyr Lys Ala Ala Arg Asn Gln Ala Ala Thr Asn Ala
            20                  25                  30

Gln Ile Leu Ala His Val
        35

<210> SEQ ID NO 11
<211> LENGTH: 39
<212> TYPE: PRT
<213> ORGANISM: Artificial Sequence
<220> FEATURE:
<223> OTHER INFORMATION: Synthetic peptide

<400> SEQUENCE: 11

Arg Val Ile Leu Ser Leu Asp Val Pro Ile Gly Leu Leu Arg Ile Leu
1               5                   10                  15

Leu Glu Gln Ala Arg Tyr Lys Ala Ala Arg Asn Gln Ala Ala Thr Asn
            20                  25                  30

Ala Gln Ile Leu Ala His Val
        35

<210> SEQ ID NO 12
<211> LENGTH: 87
<212> TYPE: PRT
<213> ORGANISM: Artificial Sequence
<220> FEATURE:
<223> OTHER INFORMATION: Synthetic peptide

<400> SEQUENCE: 12

Thr Pro Ile Pro Thr Phe Gln Leu Leu Pro Gln Asn Ser Leu Glu Thr
1               5                   10                  15

Thr Pro Ser Ser Val Thr Ser Glu Ser Ser Ser Gly Thr Thr Thr Gly
            20                  25                  30

Pro Ser Ala Ser Trp Ser Asn Ser Lys Ala Ser Pro Tyr Leu Asp Thr
        35                  40                  45

Arg Val Ile Leu Ser Leu Asp Val Pro Ile Gly Leu Leu Arg Ile Leu
    50                  55                  60

Leu Glu Gln Ala Arg Tyr Lys Ala Ala Arg Asn Gln Ala Ala Thr Asn
65                  70                  75                  80

Ala Gln Ile Leu Ala His Val
                85

<210> SEQ ID NO 13
<211> LENGTH: 40
<212> TYPE: PRT
<213> ORGANISM: Artificial Sequence
<220> FEATURE:
<223> OTHER INFORMATION: Synthetic peptide

<400> SEQUENCE: 13

Arg Ile Val Leu Ser Leu Asp Val Pro Ile Gly Leu Leu Gln Ile Leu
1               5                   10                  15

Leu Glu Gln Ala Arg Ala Arg Ala Ala Arg Glu Gln Ala Thr Thr Asn
            20                  25                  30

Ala Arg Ile Leu Ala Arg Val Gly
        35                  40

<210> SEQ ID NO 14
<211> LENGTH: 41
<212> TYPE: PRT
<213> ORGANISM: Artificial Sequence
<220> FEATURE:

<223> OTHER INFORMATION: Synthetic peptide

<400> SEQUENCE: 14

Arg Ile Val Leu Ser Leu Asp Val Pro Ile Gly Leu Leu Gln Ile Leu
1               5                   10                  15

Leu Glu Gln Ala Arg Ala Arg Ala Ala Arg Glu Gln Ala Thr Thr Asn
            20                  25                  30

Ala Arg Ile Leu Ala Arg Val Gly His
        35                  40

<210> SEQ ID NO 15
<211> LENGTH: 42
<212> TYPE: PRT
<213> ORGANISM: Artificial Sequence
<220> FEATURE:
<223> OTHER INFORMATION: Synthetic peptide

<400> SEQUENCE: 15

Arg Ile Val Leu Ser Leu Asp Val Pro Ile Gly Leu Leu Gln Ile Leu
1               5                   10                  15

Leu Glu Gln Ala Arg Ala Arg Ala Ala Arg Glu Gln Ala Thr Thr Asn
            20                  25                  30

Ala Arg Ile Leu Ala Arg Val Gly His Cys
        35                  40

<210> SEQ ID NO 16
<211> LENGTH: 86
<212> TYPE: PRT
<213> ORGANISM: Artificial Sequence
<220> FEATURE:
<223> OTHER INFORMATION: Synthetic peptide

<400> SEQUENCE: 16

Ile Pro Thr Phe Gln Leu Arg Pro Gln Asn Ser Pro Gln Thr Thr Pro
1               5                   10                  15

Arg Pro Ala Ala Ser Glu Ser Pro Ser Ala Ala Pro Thr Trp Pro Trp
            20                  25                  30

Ala Ala Gln Ser His Cys Ser Pro Thr Arg His Pro Gly Ser Arg Ile
        35                  40                  45

Val Leu Ser Leu Asp Val Pro Ile Gly Leu Leu Gln Ile Leu Leu Glu
    50                  55                  60

Gln Ala Arg Ala Arg Ala Ala Arg Glu Gln Ala Thr Thr Asn Ala Arg
65                  70                  75                  80

Ile Leu Ala Arg Val Gly
                85

<210> SEQ ID NO 17
<211> LENGTH: 87
<212> TYPE: PRT
<213> ORGANISM: Artificial Sequence
<220> FEATURE:
<223> OTHER INFORMATION: Synthetic peptide

<400> SEQUENCE: 17

Ile Pro Thr Phe Gln Leu Arg Pro Gln Asn Ser Pro Gln Thr Thr Pro
1               5                   10                  15

Arg Pro Ala Ala Ser Glu Ser Pro Ser Ala Ala Pro Thr Trp Pro Trp
            20                  25                  30

Ala Ala Gln Ser His Cys Ser Pro Thr Arg His Pro Gly Ser Arg Ile
        35                  40                  45

```
Val Leu Ser Leu Asp Val Pro Ile Gly Leu Leu Gln Ile Leu Leu Glu
     50                  55                  60

Gln Ala Arg Ala Arg Ala Ala Arg Glu Gln Ala Thr Thr Asn Ala Arg
 65                  70                  75                  80

Ile Leu Ala Arg Val Gly His
                 85

<210> SEQ ID NO 18
<211> LENGTH: 88
<212> TYPE: PRT
<213> ORGANISM: Artificial Sequence
<220> FEATURE:
<223> OTHER INFORMATION: Synthetic peptide

<400> SEQUENCE: 18

Ile Pro Thr Phe Gln Leu Arg Pro Gln Asn Ser Pro Gln Thr Thr Pro
  1               5                  10                  15

Arg Pro Ala Ala Ser Glu Ser Pro Ser Ala Ala Pro Thr Trp Pro Trp
                 20                  25                  30

Ala Ala Gln Ser His Cys Ser Pro Thr Arg His Pro Gly Ser Arg Ile
                 35                  40                  45

Val Leu Ser Leu Asp Val Pro Ile Gly Leu Leu Gln Ile Leu Leu Glu
     50                  55                  60

Gln Ala Arg Ala Arg Ala Ala Arg Glu Gln Ala Thr Thr Asn Ala Arg
 65                  70                  75                  80

Ile Leu Ala Arg Val Gly His Cys
                 85

<210> SEQ ID NO 19
<211> LENGTH: 85
<212> TYPE: PRT
<213> ORGANISM: Artificial Sequence
<220> FEATURE:
<223> OTHER INFORMATION: Synthetic peptide

<400> SEQUENCE: 19

Ile Pro Thr Phe Gln Leu Arg Pro Gln Asn Ser Pro Gln Thr Thr Pro
  1               5                  10                  15

Arg Pro Ala Ala Ser Glu Ser Pro Ser Ala Ala Pro Thr Trp Pro Trp
                 20                  25                  30

Ala Ala Gln Ser His Cys Ser Pro Thr Arg His Pro Gly Ser Arg Ile
                 35                  40                  45

Val Leu Ser Leu Asp Val Pro Ile Gly Leu Leu Gln Ile Leu Leu Glu
     50                  55                  60

Gln Ala Arg Ala Arg Ala Ala Arg Glu Gln Ala Thr Thr Asn Ala Arg
 65                  70                  75                  80

Ile Leu Ala Arg Val
                 85

<210> SEQ ID NO 20
<211> LENGTH: 825
<212> TYPE: PRT
<213> ORGANISM: Homo sapiens

<400> SEQUENCE: 20

Met Asp Pro Pro Arg Pro Ala Leu Leu Ala Leu Pro Ala Leu Leu Leu
  1               5                  10                  15

Leu Leu Leu Ala Gly Ala Arg Ala Glu Glu Glu Met Leu Glu Asn Val
                 20                  25                  30
```

-continued

Ser Leu Val Cys Pro Lys Asp Ala Thr Arg Phe Lys His Leu Arg Lys
         35                  40                  45

Tyr Thr Tyr Asn Tyr Glu Ala Glu Ser Ser Ser Gly Val Pro Gly Thr
         50                  55                  60

Ala Asp Ser Arg Ser Ala Thr Arg Ile Asn Cys Lys Val Glu Leu Glu
65                   70                  75                  80

Val Pro Gln Leu Cys Ser Phe Ile Leu Lys Thr Ser Gln Cys Ile Leu
                 85                  90                  95

Lys Glu Val Tyr Gly Phe Asn Pro Glu Gly Lys Ala Leu Leu Lys Lys
             100                 105                 110

Thr Lys Asn Ser Glu Glu Phe Ala Ala Ala Met Ser Arg Tyr Glu Leu
             115                 120                 125

Lys Leu Ala Ile Pro Glu Gly Lys Gln Val Phe Leu Tyr Pro Glu Lys
         130                 135                 140

Asp Glu Pro Thr Tyr Ile Leu Asn Ile Lys Arg Gly Ile Ile Ser Ala
145                 150                 155                 160

Leu Leu Val Pro Pro Glu Thr Glu Glu Ala Lys Gln Val Leu Phe Leu
                 165                 170                 175

Asp Thr Val Tyr Gly Asn Cys Ser Thr His Phe Thr Val Lys Thr Arg
             180                 185                 190

Lys Gly Asn Val Ala Thr Glu Ile Ser Thr Glu Arg Asp Leu Gly Gln
         195                 200                 205

Cys Asp Arg Phe Lys Pro Ile Arg Thr Gly Ile Ser Pro Leu Ala Leu
         210                 215                 220

Ile Lys Gly Met Thr Arg Pro Leu Ser Thr Leu Ile Ser Ser Ser Gln
225                 230                 235                 240

Ser Cys Gln Tyr Thr Leu Asp Ala Lys Arg Lys His Val Ala Glu Ala
                 245                 250                 255

Ile Cys Lys Glu Gln His Leu Phe Leu Pro Phe Ser Tyr Lys Asn Lys
             260                 265                 270

Tyr Gly Met Val Ala Gln Val Thr Gln Thr Leu Lys Leu Glu Asp Thr
         275                 280                 285

Pro Lys Ile Asn Ser Arg Phe Phe Gly Glu Gly Thr Lys Lys Met Gly
         290                 295                 300

Leu Ala Phe Glu Ser Thr Lys Ser Thr Ser Pro Pro Lys Gln Ala Glu
305                 310                 315                 320

Ala Val Leu Lys Thr Leu Gln Glu Leu Lys Lys Leu Thr Ile Ser Glu
                 325                 330                 335

Gln Asn Ile Gln Arg Ala Asn Leu Phe Asn Lys Leu Val Thr Glu Leu
             340                 345                 350

Arg Gly Leu Ser Asp Glu Ala Val Thr Ser Leu Leu Pro Gln Leu Ile
         355                 360                 365

Glu Val Ser Ser Pro Ile Thr Leu Gln Ala Leu Val Gln Cys Gly Gln
         370                 375                 380

Pro Gln Cys Ser Thr His Ile Leu Gln Trp Leu Lys Arg Val His Ala
385                 390                 395                 400

Asn Pro Leu Leu Ile Asp Val Val Thr Tyr Leu Val Ala Leu Ile Pro
                 405                 410                 415

Glu Pro Ser Ala Gln Gln Leu Arg Glu Ile Phe Asn Met Ala Arg Asp
             420                 425                 430

Gln Arg Ser Arg Ala Thr Leu Tyr Ala Leu Ser His Ala Val Asn Asn
         435                 440                 445

Tyr His Lys Thr Asn Pro Thr Gly Thr Gln Glu Leu Leu Asp Ile Ala

```
                    450                 455                 460
Asn Tyr Leu Met Glu Gln Ile Gln Asp Asp Cys Thr Gly Asp Glu Asp
465                 470                 475                 480

Tyr Thr Tyr Leu Ile Leu Arg Val Ile Gly Asn Met Gly Gln Thr Met
                485                 490                 495

Glu Gln Leu Thr Pro Glu Leu Lys Ser Ser Ile Leu Lys Cys Val Gln
            500                 505                 510

Ser Thr Lys Pro Ser Leu Met Ile Gln Lys Ala Ala Ile Gln Ala Leu
        515                 520                 525

Arg Lys Met Glu Pro Lys Asp Lys Asp Gln Glu Val Leu Leu Gln Thr
    530                 535                 540

Phe Leu Asp Asp Ala Ser Pro Gly Asp Lys Arg Leu Ala Ala Tyr Leu
545                 550                 555                 560

Met Leu Met Arg Ser Pro Ser Gln Ala Asp Ile Asn Lys Ile Val Gln
                565                 570                 575

Ile Leu Pro Trp Glu Gln Asn Glu Gln Val Lys Asn Phe Val Ala Ser
            580                 585                 590

His Ile Ala Asn Ile Leu Asn Ser Glu Glu Leu Asp Ile Gln Asp Leu
        595                 600                 605

Lys Lys Leu Val Lys Glu Ala Leu Lys Glu Ser Gln Leu Pro Thr Val
    610                 615                 620

Met Asp Phe Arg Lys Phe Ser Arg Asn Tyr Gln Leu Tyr Lys Ser Val
625                 630                 635                 640

Ser Leu Pro Ser Leu Asp Pro Ala Ser Ala Lys Ile Glu Gly Asn Leu
                645                 650                 655

Ile Phe Asp Pro Asn Asn Tyr Leu Pro Lys Glu Ser Met Leu Lys Thr
            660                 665                 670

Thr Leu Thr Ala Phe Gly Phe Ala Ser Ala Asp Leu Ile Glu Ile Gly
        675                 680                 685

Leu Glu Gly Lys Gly Phe Glu Pro Thr Leu Glu Ala Leu Phe Gly Lys
    690                 695                 700

Gln Gly Phe Phe Pro Asp Ser Val Asn Lys Ala Leu Tyr Trp Val Asn
705                 710                 715                 720

Gly Gln Val Pro Asp Gly Val Ser Lys Val Leu Val Asp His Phe Gly
                725                 730                 735

Tyr Thr Lys Asp Asp Lys His Glu Gln Asp Met Val Asn Gly Ile Met
            740                 745                 750

Leu Ser Val Glu Lys Leu Ile Lys Asp Leu Lys Ser Lys Glu Val Pro
        755                 760                 765

Glu Ala Arg Ala Tyr Leu Arg Ile Leu Gly Glu Glu Leu Gly Phe Ala
    770                 775                 780

Ser Leu His Asp Leu Gln Leu Leu Gly Lys Leu Leu Leu Met Asp Arg
785                 790                 795                 800

Pro Asp Ser Leu Thr Ile Pro Ala Ala Gln Ala Arg Lys Asp Ala Cys
                805                 810                 815

Thr Phe Phe Arg Asp Gly Gly Leu Pro
            820                 825

<210> SEQ ID NO 21
<211> LENGTH: 38
<212> TYPE: PRT
<213> ORGANISM: Artificial Sequence
<220> FEATURE:
<223> OTHER INFORMATION: Synthetic peptide
```

```
<400> SEQUENCE: 21

Val Ile Leu Ser Leu Asp Val Pro Ile Gly Leu Leu Arg Ile Leu Leu
1               5                   10                  15

Glu Gln Ala Arg Tyr Lys Ala Ala Arg Asn Gln Ala Ala Thr Asn Ala
            20                  25                  30

Gln Ile Leu Ala His Val
        35

<210> SEQ ID NO 22
<211> LENGTH: 39
<212> TYPE: PRT
<213> ORGANISM: Artificial Sequence
<220> FEATURE:
<223> OTHER INFORMATION: Synthetic peptide

<400> SEQUENCE: 22

Arg Val Ile Leu Ser Leu Asp Val Pro Ile Gly Leu Leu Arg Ile Leu
1               5                   10                  15

Leu Glu Gln Ala Arg Tyr Lys Ala Ala Arg Asn Gln Ala Ala Thr Asn
            20                  25                  30

Ala Gln Ile Leu Ala His Val
        35
```

UROCORTIN 2 ANALOGS AND USES THEREOF

The present application is a divisional of U.S. application Ser. No. 13/392,828, filed May 4, 2012, which is a national phase application under 35 U.S.C. §371 of International Application No. PCT/US2010/046890, filed Aug. 27, 2010, which claims benefit of U.S. Provisional Application No. 61/237,995, filed Aug. 28, 2009, the entire contents of each of which are hereby incorporated by reference.

BACKGROUND OF THE INVENTION

1. Field of the Invention

The present invention relates generally to the fields of protein chemistry, molecular biology, pharmaceutical compositions, and therapeutics. More particularly, the invention concerns methods, compositions concerning urocortin-2 analogs, and nucleic acids encoding urocortin-2 analogs.

2. Description of Related Art

Corticotropin-releasing factor (CRF) is a 41-amino acid peptide best known for its indispensable role in initiating pituitary-adrenal responses to stress, an effect mediated by type 1 CRF receptors. In addition, corticotropin-releasing factor is widely distributed in brain, and participates in the mobilization of complementary autonomic and behavioral adjustments to a variety of threatening circumstances. Corticotropin releasing factor and its related family of peptides play important roles in regulation of the hypothalamic-pituitary-adrenal axis (HPA) under basal and stress conditions. It is also believed that corticotropin-releasing factor is also involved in other neuroendocrine and paracrine responses in many tissues. Members of the CRF family integrate endocrine, autonomic and behavioral responses to stressors. These peptides may also be implicated in the control of appetite, arousal, and cognitive functions. Severe psychological and physiological consequences can occur as a result of the long term effects of stress, such as anxiety disorders, anorexia nervosa and melancholic depression.

Corticotropin-releasing factor family members mediate their biological actions by specifically binding to CRF receptors with high affinities. CRF receptors are G-protein coupled receptors that act through adenylate cyclase and are structurally related to the secretin family. This family also includes GRF, VIP, PTH, and the Calcitonin receptor. CRF-R1 receptor is distributed throughout the brain and is found in sensory and motor relay sites. The CRF-R2α is distributed in lateral septum, ventral medial hypothalamus, nucleus of the solitary tract and the dorsal raphe nucleus, which are areas where CRF-R1 is expressed very little or not at all. The CRF-R2β is found mostly in peripheral sites including the heart, blood vessels, gastrointestinal tract, epididymis, lung and skin. The pharmacology of the two types of receptors differs in that corticotropin-releasing factor has a low affinity for CRF-R2 but a high affinity for CRF-R1. Other related peptides such as carp urotensin, frog sauvagine, and urocortin have a high affinity for CRF-R2. CRF-R2 knockout mice demonstrate an increased anxiety-like behavior caused by hypersensitivity to stressors.

A mammalian CRF-related neuropeptide, urocortin (Ucn), binds with high affinity to both known CRF receptor types, whereas CRF is bound in a highly preferential manner by CRF-R1. Centrally administered urocortin is more potent than CRF in suppressing appetite but less so in generating acute anxiety-like effects and generalized behavioral activation. This has been taken to indicate that urocortin might mediate some stress-related effects attributed initially to CRF, at least in part by serving as an endogenous ligand for CRF-R2. Urocortin has been proposed as a therapeutic agent in heart disease (see, e.g., Raddino et al., 2007; Davidson et al., 2009).

Urocortin 2 (Ucn 2), one of the CRF peptide family members, is thought to be an endogenous ligand for CRF type 2 receptor (CRF-R2). The roles of urocortin 2 in the body are diverse, and include involvement in affective disorders, stimulation of the immune system, and cardio-protection (Lawrence and Latchman, 2006). Therapeutic application of urocortin 2 is limited because of the limited water solubility of the urocortin 2 peptide. Therefore, there is the need for active urocortin 2 analogs that have improved water solubility.

SUMMARY OF THE INVENTION

The present invention is in part based on the identification of analogs of urocortin 2 that have the surprising and unexpected ability to stimulate intracellular cAMP production in cells in a manner similar to urocortin 2, yet have improved water solubility compared to urocortin 2. Improved water solubility will lead to greater therapeutic application of urocortin 2 analogs in the treatment and prevention of diseases and health-related conditions involving the hypothalamic-pituitary-adrenal axis.

Some embodiments of the present invention include urocortin analogs that are isolated polypeptides of formula (I):

$$X_1\text{-}X_2\text{-}X_3\text{-}X_4\text{-}X_5\text{-}X_6 \qquad (I)$$

wherein $X_1$ is either absent or a polypeptide having 1-200 residues; $X_2$ is absent or 1-20 amino acid residues that are each individually selected from either arginine (R) or lysine (K); $X_3$ is SEQ ID NO:1, SEQ ID NO:19, SEQ ID NO:21, or SEQ ID NO:22; $X_4$ is either absent, G, GH, or GHC; $X_5$ is absent or 1-20 amino acid residues that are each individually selected from either arginine (R) or lysine (K); $X_6$ is either absent or a polypeptide having 1-200 residues.

Some embodiments of the present invention include the proviso that if $X_3$ is SEQ ID NO:1, $X_4$, $X_5$, $X_6$ are all absent, then $X_2$ is not absent, further provided that if $X_3$ is SEQ ID NO:19, $X_5$ is absent and $X_6$ is absent, then $X_4$ is G, GH, or GHC. In particular embodiments, $X_3$ is SEQ ID NO:1. In further particular embodiments, $X_3$ is SEQ ID NO:19. In further particular embodiments, $X_2$ is arginine (R).

In particular embodiments, $X_1$ and $X_2$ are absent, $X_3$ is SEQ ID NO:1, $X_4$ is glycine, and $X_6$ is absent.

In other embodiments, $X_1$ is absent, $X_3$ is SEQ ID NO:1, $X_4$ is absent, $X_5$ is absent, $X_6$ is absent, and the polypeptide is further defined as being amidated at the C-terminus.

In further embodiments, $X_1$ and $X_2$ are absent, $X_3$ is SEQ ID NO:19, $X_4$ is glycine, and $X_6$ is absent.

In other embodiments, the polypeptide of formula (I) is further defined as being amidated at the C-terminus. Amidation can be by any method known to those of ordinary skill in the art.

$X_2$ and $X_5$ may be a consecutive series of 2, 3, 4, 5, 6, 7, 8, 9, 10, 11, 12, 13, 14, 15, 16, 17, 18, 19, 20 amino acids that are either R and K. In particular embodiments, $X_2$ and/or $X_5$ include 2 amino acid residues. In specific embodiments, the amino acid residue is arginine (R).

Other embodiments of the present invention include any of the foregoing peptides that are amidated at the C-terminus. Some embodiments include a C residue at the N-terminus and a C residue at the C-terminus.

Other embodiments concern urocortin 2 or a peptide derived from urocortin 2 that is amidated at the C-terminus.

Other analogs of urocortin 2 include any peptide derived from a prohormone of urocortin 2 that is amidated at the C-terminus. In some embodiments the urocortin 2 analog is a full-length prohormone of urocortin 2 that is amidated at the C-terminus. The prohormone of urocortin 2 or urocortin may be from any species. In particular embodiments, the urocortin 2 or prohormone of urocortin 2 is from human or mouse. In specific embodiments, the urocortin analog is SEQ ID NO:9 or SEQ ID NO:12.

Other embodiments of the present invention include analogs of urocortin 2 that are isolated polypeptides of formula I: $Z_1$-$Z_2$, where $Z_1$ is (i) one amino acid selected from the group of amino acids consisting of R and K or (ii) a consecutive series of amino acids selected from the group consisting of R and K; and $Z_2$ comprises a urocortin 2 or prohormone of urocortin 2 amino acid sequence. For example, in some embodiments Z2 is IVLSLDVPIGLLQ-ILLEQARARAAREQATTNARILARV (SEQ ID NO:1), SEQ ID NO:19, SEQ ID NO:21, or SEQ ID NO:22, provided that the carboxy terminus of $Z_1$ is covalently attached to the N-terminus of SEQ ID NO:1. The analog may optionally be amidated at the C-terminus.

Other embodiments of the present invention include analogs that comprises a urocortin 2 or prohormone of urocortin 2 amino acid sequence that includes G, GH, or GHC attached to the C-terminus of the urocortin 2 or prohormone of urocortin 2 amino acid sequence.

A table of amino acid abbreviations is provided in the specification below; the single letter abbreviations for amino acids will be used throughout this disclosure. The isolated polypeptides of the present invention a consecutive series of 2, 3, 4, 5, 6, 7, 8, 9, 10, 11, 12, 13, 14, 15, 16, 17, 18, 19, 20, 25, 30, 35, 40, 45, 50, or more amino acids or any range of amino acids derivable therein. For example, $Z_1$ may be 2-30 consecutive amino acids in length, 2-20 consecutive amino acids in length, 2-10 consecutive amino acids in length, or 2-5 consecutive amino acids in length. In particular embodiments, $Z_1$ consists of one amino acid selected from the group consisting of R and K. In a specific embodiment, $Z_1$ is R (arginine). $Z_2$ may include one or a series of consecutive amino acids attached to the C-terminus. For example, the C-terminus may include 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000 or any range of amino acids derivable therein. For example, there may be 2-500, 2-400, 2-300, 2-200, 2-100, 2-50, 2-20, or 2-10 consecutive amino acids attached to the C-terminus of SEQ ID NO:1. In specific embodiments, $Z_1$ is SEQ ID NO:1 (i.e., with no amino acids attached to the C-terminus of SEQ ID NO:1). In particular embodiments, the isolated polypeptide is SEQ ID NO:2, SEQ ID NO:3, or SEQ ID NO:4.

In some embodiments, the C-terminus or the N-terminus of the polypeptide is protected.

In particular embodiments, the C-terminus of any of the foregoing polypeptides is amidated. Binding of any moiety known to form an amide when reacted with the carboxy terminus of a polypeptide is contemplated by the present invention.

In some embodiments, the isolated polypeptide of the present invention may have a protected C-terminus or a protected N-terminus. Thus, for example, a protecting group may be attached to the N-terminus or C-terminus of the polypeptide of the present invention. In some embodiments, the C-terminus is amidated. In some embodiments, an amino protecting agent is used to protect the N-terminus.

Some embodiments of the instant invention include analogs of urocortin as set forth herein that have an acylated N-terminus. This protein acylation may be used to link a molecule such as fatty acid at the N-terminus of the protein to protect the polypeptide from enzymatic degradation or to change various properties of the protein such as its hydrophilicity/hydrophobicity. These modifications may be used to alter the duration or bioavailability of the protein in vivo.

In some embodiments, the isolated polypeptides of the present invention can be conjugated to complexing agents for radionuclides. As mentioned, conjugation between the complexing agent and the polypeptides set forth herein may take place via any method and chemical linkage known to those of skill in the art. A protecting group may be removed prior to conjugation to a complexing agent. The complexing agent may be a chelator. The radionuclide may be any radionuclide known to those of ordinary skill in the art. In non-limiting examples, the metal ion may be selected from the group consisting of a technetium ion, a copper ion, an indium ion, a thallium ion, a gallium ion, an arsenic ion, a rhenium ion, a holmium ion, a yttrium ion, a samarium ion, a selenium ion, a strontium ion, a gadolinium ion, a bismuth ion, an iron ion, a manganese ion, a lutecium ion, a cobalt ion, a platinum ion, a calcium ion and a rhodium ion. The radionuclide-labeled analogs can be used for imaging such as scintigraphy.

The isolated polypeptides of the present invention may be modified to contain a label, such as radioactive elements, enzymes, chemicals that fluoresce when exposed to ultraviolet light, and others. A number of fluorescent materials are known and can be utilized as labels. These include, for example, fluorescein, rhodamine, auramine, Texas Red, AMCA blue and Lucifer Yellow. The resulting labeled urocortin 2 analogs can be used to identify cells expressing CRF receptors for biological assays. Alternatively, the polypeptides set forth herein may be linked to a toxin molecule. The resulting toxic conjugate can be used for the targeted destruction of CRF receptor-bearing cells.

In specific embodiments, the polypeptide includes SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:13, SEQ ID NO:14, SEQ ID NO:15, SEQ ID NO:16, SEQ ID NO:17, or SEQ ID NO:18.

The present invention also contemplates chimeric polypeptide that include a first amino acid sequence that is a recombinant urocortin 2 analog and a second amino acid sequence, wherein the second amino acid sequence is a therapeutic amino acid sequence. In some embodiments, the second amino acid sequence enhances the bioavailability of the first amino acid sequence. For example the second amino acid sequence may enhance bioavailability across the blood-brain barrier. For example, the second amino acid sequence may be selected from the group consisting of a low density lipoprotein receptor binding domain of apolipoprotein B, an Fc amino acid sequence, or a toxin. Non-limiting examples of toxins include gelonin, dodecandrin, tricosanthin, tricokirin, bryodin, mirabilis antiviral protein, barley ribosome-inactivating protein (BRIP), pokeweed antiviral protein (PAPs), saporin, luffin, momordin, ricin, abrin, diphtheria toxin A, pertussis toxin A subunit, *E. coli* enterotoxin toxin A subunit, cholera toxin (CTX) and *Pseudomonas* toxin c-terminal. In some embodiments, the chimeric polypeptide is a fusion protein encoded by a single polynucleotide. Polynucleotides encoding the chimeric polypeptides set forth herein are also contemplated. Methods of treating disease, compositions, and kits employing the chimeric polypeptides and polynucleotides of the present invention are also contemplated.

Further embodiments of the present invention include a recombinant nucleic acid that includes a nucleic acid segment encoding any of the polypeptides of the present invention. In specific embodiments, the polypeptide includes SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:13, SEQ ID NO:14, SEQ ID NO:15, SEQ ID NO:16, SEQ ID NO:17, or SEQ ID NO:18. In particular embodiments, $X_6$ is —OH.

Other aspects of the invention concern recombinant nucleic acids encoding any of the aforementioned polypeptides. The nucleic acids may optionally encode one or more additional amino acid residues. The nucleic acid may optionally be comprised in a vector. Non-limiting examples of vectors include nanoparticles comprising a lipid, viral vectors, and cells. The vector may further include regulatory elements necessary for expression of said nucleic acid sequence in a cell. In particular embodiments, the vector may be a viral vector. For example, the viral vector may be an adenoviral vector, a lentiviral vector, or an adeno-associated viral vector. The vector also includes host cells transfected with vectors as set forth herein. Non-limiting examples of host cells include a bacterial cell, a mammalian cell, a plant cell, or an insect cell. As used herein, the term "host" is meant to include not only prokaryotes but also eukaryotes such as yeast, plant and animal cells. A recombinant DNA molecule or gene that encodes a polypeptide of the present invention can be used to transform a host using any of the techniques commonly known to those of ordinary skill in the art. Prokaryotic hosts may include *E. coli, S. tymphimurium, S. marcescens* and *B. subtilis*. Non-limiting examples of eukaryotic hosts include yeasts such as *P. pastoris*, mammalian cells and insect cells.

Other aspects of the invention concern pharmaceutical compositions that include any of the aforementioned polypeptides or recombinant nucleic acids, and a pharmaceutically acceptable carrier. Non-limiting examples of pharmaceutically acceptable carriers include water or normal saline.

The present invention also concerns methods of treating a pathophysiological state (disease or health-related condition) in a subject, involving administering to the subject a pharmaceutical composition that includes any of the polypeptides, chimeric polypeptides, or polynucleotides as set forth herein and a pharmaceutically acceptable carrier. The subject may be any subject. In particular embodiments, the subject is a mammal. Non-limiting examples of mammals include a human, a primate, a horse, a cow, a sheep, a pig, a dog, a cat, a rat, or a mouse. In specific embodiments, the mammal is a human. The human may be a patient with a pathophysiological state or at risk of developing a pathophysiological state. The pathophysiological state is any pathophysiological state known to those of ordinary skill in the art. In some embodiments, the pathophysiological state is a disease or health-related condition that involves the HPA. Non-limiting examples of pathophysiological states include affective disorders, disorders of elevated body temperature, appetite dysfunction, obesity, abnormalities of glucose metabolism, heart disease, stress, anxiety, and undesirably low levels of ACTH secretion. Non-limiting examples of affective disorders include depression, manic-depressive disease, and schizophrenia. Non-limiting examples of disorders of elevated body temperature include infections and malignancies. Non-limiting examples of heart disease include congestive heart failure, myocardial infarction, angina, and arrhythmias. Non-limiting examples of abnormalities of glucose metabolism include impaired glucose tolerance, hyperglycemia, and diabetes.

Treatment of any pathophysiological state wherein urocortin analogues are known or suspected to be of value is contemplated by the present invention. Non-limiting examples of pathophysiological states include high body temperature, appetite dysfunction, congestive heart failure, stress, anxiety, and undesirably low levels of ACTH secretion.

Host cells transfected with a vector of the present invention are also contemplated by the present invention. For example, the host cell may be a bacterial cell, a mammalian cell, a plant cell, or an insect cell.

Kits that include a sealed container that includes a pharmaceutically acceptable composition of any of the polypeptides or nucleic acids of the present invention are also contemplated. The kit may include any number of additional components as discussed in the specification below. In particular embodiments, the kit further includes a secondary pharmaceutical agent that can be applied in the treatment of a pathophysiological state.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device and/or method being employed to determine the value.

As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF ILLUSTRATIVE EMBODIMENTS

The present invention is partly based on the identification of analogs of urocortin 2 that have a similar ability to stimulate cAMP production in cells as compared to urocortin 2, but which are surprisingly and unexpectedly more water soluble than urocortin 2. This increased water solubility allows for increased pharmaceutical application of these agents, and the improved treatment of a variety of pathophysiological states that implicate the HPA axis.

A. Urocortin 2 Analogs

The present invention includes polypeptides that are analogs of urocortin 2 as discussed above. All amino-acid residue sequences are represented herein by formulae whose left and right orientation is in the conventional direction of amino-terminus to carboxy-terminus and by single letter abbreviations. Table 1 sets forth a table of the common amino acids and abbreviations known to those of ordinary skill in the art.

TABLE 1

Amino Acids

| Amino Acids | 3-Letter Abbreviation | Single Letter Abbreviation |
| --- | --- | --- |
| Alanine | Ala | A |
| Cysteine | Cys | C |
| Aspartic acid | Asp | D |
| Glutamic acid | Glu | E |
| Phenylalanine | Phe | F |
| Glycine | Gly | G |
| Histidine | His | H |
| Isoleucine | Ile | I |
| Lysine | Lys | K |
| Leucine | Leu | L |
| Methionine | Met | M |
| Asparagine | Asn | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |
| Tyrosine | Tyr | Y |

It should be noted that a dash at the beginning or end of an amino acid residue sequence indicates a peptide bond to a further sequence of one or more amino-acid residues.

The amino acids described herein are preferred to be in the "L" isomeric form. However, residues in the "D" isomeric form can be substituted for any L-amino acid residue, as long as the desired functional property of immunoglobulin binding is retained by the polypeptide. NH.sub.2 at the amino-terminus refers to the free amino group present at the amino terminus of a polypeptide. —OH at the carboxy terminus refers to the free carboxy group present at the carboxy terminus of a polypeptide. NH.sub.2 at the carboxy terminus refers to a C-terminal amide present at the carboxy terminus of a polypeptide.

Nonstandard amino acids may be incorporated into proteins by chemical modification of existing amino acids or by artificial synthesis of a protein. A nonstandard amino acid refers to an amino acid that differs in chemical structure from the twenty standard amino acids encoded by the genetic code. Post-translational modification in vivo can also lead to the presence of a nonstandard or amino acid derivative in a protein. The N-terminal NH.sub.2 and C-terminal COOH groups of a protein can also be modified by natural or artificial post-translational modification of a protein.

Various embodiments of the present invention pertain to methods for treating or preventing a pathophysiological state in a subject comprising a pharmaceutical composition comprising a polypeptide or nucleic acid encoding a polypeptide of the present invention as set forth herein.

As used herein, the term "polypeptide" is a consecutive amino acid segment of greater than two amino acids in length. As set forth herein, the polypeptides of the present invention comprise SEQ ID NO:1. The polypeptides set forth herein can include one or more amino acids attached to the N-terminus of SEQ ID NO:1, wherein the amino acids are hydrophilic amino acids as discussed above. Further, the polypeptides set forth herein can include one or more consecutive amino acids attached to the C-terminus of SEQ ID NO:1. For example, the polypeptide can be a polypeptide that includes 4, 5, 10, 15, 20, 25, 30, 50, 100, 200, 300, 400, 500, 1000 or any number of consecutive amino acids attached to the C-terminus of SEQ ID NO:1. The polypeptide may include 0, 1, 2, 3, 4, 5, 10, 15, 20, 25, 30, 35, 40, 50, 100, or more consecutive hydrophilic amino acids attached to the N-terminus of SEQ ID NO:1. One of ordinary skill in the art would understand how to generate a polypeptides of the present invention in view of the disclosure using any of a number of experimental methods well-known to those of skill in the art.

Also encompassed in the present invention are polypeptide variants of the polypeptides as set forth herein. For example, the polypeptide variants may include a certain amount of sequence identity compared to the polypeptides of the present invention. Thus, for example, polypeptide variants may be variants that have an amino acid identity of 80%, 85%, 90%, 95%, 98%, or 99% or more, or any range of amino acid identify derivable therein, with (1) a polypeptide that consists of SEQ ID NO:1 with a R (arginine) moiety attached to the N-terminus of SEQ ID NO:1, (2) SEQ ID NO:2, (3) SEQ ID NO:3, or (4) SEQ ID NO:4.

The present invention may utilize polypeptides purified from a natural source or obtained from recombinantly-produced material. Those of ordinary skill in the art would know how to produce these polypeptides from recombinantly-produced material. This material may use the 20 common amino acids in naturally synthesized proteins, or one or more modified or unusual amino acids. Generally, "purified" will refer to a composition that has been subjected to fractionation to remove various other proteins, polypeptides, or peptides. Purification may be substantial, in which the polypeptide or equivalent is the predominant species, or to homogeneity, which purification level would permit accurate degradative sequencing.

Amino acid sequence mutants also are encompassed by the present invention, and are included within the definition of "polypeptide variants." Amino acid sequence variants of the polypeptide can be substitutional mutants or insertional mutants. Insertional mutants typically involve the addition of material at a non-terminal point in the peptide. This may include the insertion of a few residues, or simply a single residue. The added material may be modified, such as by methylation, acetylation, and the like. Alternatively, additional residues may be added to the N-terminal or C-terminal ends of the peptide.

Amino acid substitutions are generally based on the relative similarity of the amino acid side-chain substituents, or for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

B. Chimeric Proteins

The present invention also concerns chimeric proteins that include a first amino acid sequence that is a urocortin 2 analog and a second amino acid sequence attached to the N or C-terminus of the urocortin 2 analog. The second amino acid sequence may be any amino acid sequence that includes 2 or more amino acid residues. In some embodiments, the second amino acid sequence is a therapeutic peptide or polypeptide. Examples include amino acid sequences that enhance biological activity of the urocortin 2 analog. Examples include amino acid sequences that facilitate penetration of the urocortin 2 analog across the blood-brain barrier. One example is the low-density lipoprotein receptor binding domain of apolipoprotein B (Spencer and Verma, 2007). In specific embodiments, a lentivirus vector system is used to delivery a fusion protein that includes a urocortin 2 analog fused to a low-density lipoprotein receptor binding domain of apolipoprotein A. The amino acid sequence of the low-density lipoprotein receptor binding domain of apolipoprotein A includes amino acids 3371-3409 of human ApoB (GenBank Accession Number AAH51278), herein after SEQ ID NO:20. Other specific examples of therapeutic amino acid sequences that facilitate translocation of amino acid sequences across cell membranes include the HIV TAT sequence (Nagahara et al., 1998), the third helix of the Antennapedia homeodomain (Antp) (Derossi et al., 1994), and the HSV-1 structural protein VP22 (Elliott and O'Hare, 1997). In other embodiments, the second amino acid sequence is an agent that increases duration of action of the urocortin-2 polypeptide. One non-limiting example is an amino acid sequence encoding Fc or a fragment thereof. Other class of possible second amino acid sequences include agents that can kill cells. For example, the second amino acid sequence may be a toxin, such as gelonin, dodecandrin, tricosanthin, tricokirin, bryodin, mirabilis antiviral protein, barley ribosome-inactivating protein (BRIP), pokeweed antiviral proteins (PAPs), saporins, luffins, momordins, ricin, abrin, diphtheria toxin A, pertussis toxin A subunit, *E. coli* enterotoxin toxin A subunit, cholera toxin (CTX) and *Pseudomonas* toxin c-terminal.

The two moieties of the chimeric protein produced by synthetic or recombinant methods may be conjugated by linkers according to methods well known in the art (Brinkmann and Pastan, 1994). As used herein, a "linker" is a chemical or peptide or polypeptide that links a first amino acid sequence with a second amino acid sequence. Non-limiting examples of linkers include flexible polylinkers, such as one composed of a pentamer of four consecutive glycine resides with a serine residue at the C-terminus. Such a linker may be repeated 1 or more times. Any other linker known to those of ordinary skill in the art is contemplated by the present invention.

It is contemplated that cross-linkers may be implemented to fuse the first amino acid sequence and the second amino acid sequence. Cross-linking reagents are used to form molecular bridges that tie together functional groups of two different molecules. To link two different polypeptides in a step-wise manner, hetero-bifunctional cross-linkers can be used that eliminate unwanted homopolymer formation. Bifunctional cross-linking reagents have been extensively used for a variety of purposes including preparation of affinity matrices, modification and stabilization of diverse structures, identification of binding sites, and structural studies.

In some embodiments, the chimeric protein is further defined as a fusion protein. A "fusion protein" as used herein refers to a polypeptide encoded by a single recombinant polynucleotide encoding the chimeric protein. The chimeric polypeptides set forth herein may comprises a sequence of any number of additional amino acid residues at either the N-terminus or C-terminus of the chimeric polypeptide.

"Chemical derivative" refers to a subject polypeptide having one or more residues chemically derivatized by reaction of a functional side group. Such derivatized polypeptides include, for example, those in which free amino groups have been derivatized to form amine, p-toluene sulfonyl groups, carbobenzoxy groups, t-butyloxycarbonyl groups, chloroacetyl groups, or formyl groups. Free carboxyl groups may be derivatized to form salts, methyl and ethyl esters or other types of esters or hydrazides. Chemical derivatives may include those peptides which contain one or more naturally occurring amino acids derivatives of the twenty standard amino acids. For example, 4-hydroxyproline may be substituted for serine; and ornithine may be substituted for lysine. Peptides embraced by the present invention also include peptides having one or more residue additions and/or deletions relative to the specific peptide whose sequence is shown herein, so long as the modified peptide maintains the requisite biological activity.

Additional information regarding urocortin 2 and urocortins can be found in U.S. Patent Application Publication Nos. 20080161235, 20070191592, 20070042954, 20050191650, and 20030032587, and U.S. Pat. Nos. 7,507,794, 7,488,865, 7,459,427, 7,223,846, 7,141,546, 6,838,274, 6,353,152, and 6,214,797, each of the foregoing of which is herein specifically incorporated by reference in its entirety.

C. Polynucleotides Encoding Urocortin 2 Analogs

In certain embodiments the present invention concerns polynucleotides encoding urocortin 2 or analogs of urocortin 2, and uses of such polynucleotides in methods as set forth herein.

The polynucleotide may include additional nucleic acid sequences that do not encode a urocortin 2 analog. The polynucleotides may be derived from genomic DNA, i.e., cloned directly from the genome of a particular organism. The polynucleotide may be a DNA or a RNA.

In some embodiments, the polynucleotides may be complementary DNA (cDNA). cDNA is DNA prepared using messenger RNA (mRNA) as a template. Thus, a cDNA does not contain any interrupted coding sequences and usually contains almost exclusively the coding region(s) for the corresponding protein. In other embodiments, the polynucleotide may be produced synthetically.

It may be advantageous to combine portions of the genomic DNA with cDNA or synthetic sequences to generate specific constructs. For example, where an intron is desired in the ultimate construct, a genomic clone will need to be used. Introns may be derived from other genes in addition to urocortin 2. The cDNA or a synthesized polynucleotide may provide more convenient restriction sites for the remaining portion of the construct and, therefore, would be used for the rest of the sequence.

The polynucleotides encoding urocortin 2 analogs may be naturally-occurring homologous polynucleotide sequences from other organisms. A person of ordinary skill in the art would understand that commonly available experimental techniques can be used to identify or synthesize polynucleotides encoding urocortin analogs. The present invention also encompasses chemically synthesized mutants of these sequences.

Another kind of sequence variant results from codon variation. Because there are several codons for most of the 20 normal amino acids, many different DNAs can encode a urocortin 2 analog. One of ordinary skill in the art would understand these variants.

Allowing for the degeneracy of the genetic code, sequences that have between about 50% and about 75%, or between about 76% and about 99% of nucleotides that are identical to urocortin 2 may be considered as urocortin 2 analogs of the present invention. Sequences that are within the scope the polynucleotides used in the methods set forth herein are those that are capable of base-pairing with a polynucleotide segment set forth above under intracellular conditions.

As stated above, the polynucleotides employed in the methods set forth herein may be full length genomic or cDNA copies, or large fragments thereof. The present invention also may employ shorter oligonucleotides. Sequences of 12 bases long should occur only once in the human genome and, therefore, suffice to specify a unique target sequence.

In certain embodiments, one may wish to employ constructs which include other elements, for example, those which include C-5 propyne pyrimidines. Oligonucleotides which contain C-5 propyne analogues of uridine and cytidine have been shown to bind RNA with high affinity (Wagner et al., 1993).

For those urocortin 2 analogs with a C-terminal amide, the corresponding nucleic acid sequence would be a nucleic acid sequence encoding Gly-X or Gly-X-X, where X is either Arg or Lys.

In some embodiments, the polynucleotides set forth herein encode a chimeric protein that includes a first amino acid sequence that is a urocortin 2 analog and a second amino acid sequence, as discussed above.

D. Pharmaceuticals and Methods for the Treatment of Disease

In additional embodiments, the present invention concerns formulation of one or more of the polynucleotides and/or polypeptides disclosed herein in pharmaceutically-acceptable carriers for administration to a cell, tissue, animal, patient, or subject either alone, or in combination with one or more other modalities of therapy.

Aqueous pharmaceutical compositions of the present invention will have an effective amount of a polypeptide or polynucleotide of the present invention. Such compositions generally will be dissolved or dispersed in a pharmaceutically acceptable carrier or aqueous medium. An "effective amount," for the purposes of therapy, is defined as that amount that causes a clinically measurable difference in the condition of the subject. This amount will vary depending on the substance, the condition of the patient, the type of treatment, etc.

The phrases "pharmaceutically or pharmacologically acceptable" refer to molecular entities and compositions that do not produce a significant adverse, allergic or other untoward reaction when administered to an animal, or human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredients, its use in the therapeutic compositions is contemplated.

In addition to the compounds formulated for parenteral administration, such as those for intravenous or intramuscular injection, other pharmaceutically acceptable forms include, e.g., tablets or other solids for oral administration; time release capsules; and any other form currently used, including creams, lotions, inhalants and the like.

The active compounds of the present invention will often be formulated for parenteral administration, e.g., formulated for injection via the intravenous, intramuscular, subcutaneous, or even intraperitoneal routes. The preparation of an aqueous composition that contains a polypeptide or polynucleotide of the present invention alone or in combination with a conventional therapeutic agent as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In many cases, the form must be sterile and must be fluid to the extent that easy syringability exists. It must be stable under the conditions for manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

The composition can be administered to the subject using any method known to those of ordinary skill in the art. For example, a pharmaceutically effective amount of the composition may be administered intravenously, intracerebrally, intracranially, intrathecally, into the substantia nigra or the region of the substantia nigra, intradermally, intraarterially, intraperitoneally, intralesionally, intratracheally, intranasally, topically, intramuscularly, intraperitoneally, subcutaneously, orally, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (Remington's, 1990).

In particular embodiments, the composition is administered to a subject using a drug delivery device. Any drug delivery device is contemplated for use in delivering a pharmaceutically effective amount of a polypeptide or polynucleotide of the present invention.

For parenteral administration in an aqueous solution, for example, the solution should be suitably buffered if necessary and the liquid diluent first rendered isotonic with sufficient saline, mannitol or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" (1980)). Some variation in dosage will necessarily occur depending on the condition of the subject being treated. The person responsible for administration will, in any event, determine the appropriate dose for the individual subject.

In certain aspects of the methods of the invention, the route the therapeutic composition is administered may be by parenteral administration. The parenteral administration may be intravenous injection, subcutaneous injection, intramuscular injection, intramedullary injection, ingestion or a combination thereof. In certain aspects, the composition comprising a polypeptide or polynucleotide of the present invention is administered from about 0.1 to about 10 microgram/kg/body weight per dose. In certain aspects, the composition is administered from about 1 to about 5 microgram/kg/body weight per dose. In certain aspects, the composition is administered from about 1.2 to about 3.6 microgram/kg/body weight per dose. In certain aspects, the composition is administered from about 1.2 to about 2.4 microgram/kg/body weight per dose. In preferred aspects, the amount of polypeptide or polynucleotide of the present invention administered per dose may be about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3 5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, about 10.0, or more micrograms/kg/body.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

The term "alimentary delivery" refers to the administration, directly or otherwise, to a portion of the alimentary canal of an animal. The term "alimentary canal" refers to the tubular passage in an animal that functions in the digestion and absorption of food and the elimination of food residue, which runs from the mouth to the anus, and any and all of its portions or segments, e.g., the oral cavity, the esophagus, the stomach, the small and large intestines and the colon, as well as compound portions thereof such as, e.g., the gastrointestinal tract. Thus, the term "alimentary delivery" encompasses several routes of administration including, but not limited to, oral, rectal, endoscopic and sublingual/buccal administration. A common requirement for these modes of administration is absorption over some portion or all of the alimentary tract and a need for efficient mucosal penetration of the agent so administered.

In certain applications, the pharmaceutical compositions disclosed herein may be delivered via oral administration to an animal, patient, or subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active components may even be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup of elixir may contain the active component sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

Therapeutics administered by the oral route can often be alternatively administered by the lower enteral route, i.e., through the anal portal into the rectum or lower intestine. Rectal suppositories, retention enemas or rectal catheters can be used for this purpose and may be preferred when patient compliance might otherwise be difficult to achieve (e.g., in pediatric and geriatric applications, or when the patient is vomiting or unconscious). Rectal administration may result in more prompt and higher blood levels than the oral route, but the converse may be true as well (Harvey, 1990). Because about 50% of the therapeutic that is absorbed from the rectum will bypass the liver, administration by this route significantly reduces the potential for first-pass metabolism (Benet et al., 1996).

The term "parenteral delivery" refers to the administration of a therapeutic of the invention to an animal, patient or subject in a manner other than through the digestive canal. Means of preparing and administering parenteral pharmaceutical compositions are known in the art (see, e.g., Avis, 1990).

Intraluminal administration, for the direct delivery of a therapeutic to an isolated portion of a tubular organ or tissue (e.g., such as an artery, vein, ureter or urethra), may be desired for the treatment of patients with diseases or conditions afflicting the lumen of such organs or tissues. To effect this mode of administration, a catheter or cannula is surgically introduced by appropriate means. After isolation of a portion of the tubular organ or tissue for which treatment is sought, a composition comprising a therapeutic of the invention is infused through the cannula or catheter into the isolated segment. After incubation for from about 1 to about 120 minutes, during which the therapeutic is taken up or in contact with the cells of the interior lumen of the vessel, the infusion cannula or catheter is removed and flow within the tubular organ or tissue is restored by removal of the ligatures which effected the isolation of a segment thereof (Morishita et al., 1993). Therapeutic compositions of the invention may also be combined with a biocompatible matrix, such as a hydrogel material, and applied directly to vascular tissue in vivo.

Intraventricular administration, for the direct delivery of a therapeutic to the brain of a patient, may be desired for the treatment of patients with diseases or conditions afflicting the brain. One method to affect this mode of administration, a silicon catheter is surgically introduced into a ventricle of the brain of a human patient, and is connected to a subcutaneous infusion pump (Medtronic Inc., Minneapolis, Minn.) that has been surgically implanted in the abdominal region (Zimm et al., 1984; Shaw, 1993). The pump is used to inject the therapeutic and allows precise dosage adjustments and variation in dosage schedules with the aid of an external programming device. The reservoir capacity of the pump is 18-20 mL and infusion rates may range from 0.1 mL/h to 1 mL/h. Depending on the frequency of administration, ranging from daily to monthly, and the dose of drug to be administered, ranging from 0.01-100 microgram per kg of body weight, the pump reservoir may be refilled at 3-10 week intervals. Refilling of the pump may be accomplished by percutaneous puncture of the self-sealing septum of the pump.

Intrathecal drug administration, for the introduction of a therapeutic into the spinal column of a patient may be desired for the treatment of patients with diseases of the central nervous system. To effect this route of administration, a silicon catheter may be surgically implanted into the L3-4 lumbar spinal interspace of a human patient, and is connected to a subcutaneous infusion pump which has been surgically implanted in the upper abdominal region (Luer and Hatton, 1993; Ettinger et al., 1978; Yaida et al., 1995). The pump is used to inject the therapeutic and allows precise dosage adjustments and variations in dose schedules with the aid of an external programming device. The administered dose may be similar to that for intraventricular administration.

To effect delivery to areas other than the brain or spinal column via this method, the silicon catheter is configured to connect the subcutaneous infusion pump to, e.g., the hepatic artery, for delivery to the liver (Kemeny et al., 1993).

Vaginal delivery provides local treatment and avoids first pass metabolism, degradation by digestive enzymes, and potential systemic side-effects. Vaginal suppositories (Remington's Pharmaceutical Sciences, 18th Ed., 1990) or topical ointments can be used to effect this mode of delivery.

In certain embodiments, the inventors contemplate the use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, or a nanoparticle or the like.

Such formulations may be preferred for the introduction of pharmaceutically-acceptable formulations of the nucleic acids or constructs disclosed herein. The formation and use of liposomes is generally known to those of skill in the art (see for example, Couvreur et al., 1977; Lasic, 1998; which describes the use of liposomes and nanocapsules in the targeted antibiotic therapy for intracellular bacterial infections and diseases). Recently, liposomes were developed with improved serum stability and circulation half-times (Gabizon and Papahadjopoulos, 1988; Allen and Choun, 1987; U.S. Pat. No. 5,741,516, specifically incorporated herein by reference in its entirety). Further, various methods of liposome and liposome like preparations as potential drug carriers have been reviewed (Takakura, 1998; Chandran et al., 1997; Margalit, 1995; U.S. Pat. Nos. 5,567,434; 5,552,157; 5,565,213; 5,738,868 and 5,795,587, each specifically incorporated herein by reference in its entirety).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 .mu.m. Sonication of MLVs results in the formation of small unilamellar vesicles (SUVs) with diameters in the range of 200 to 500 ANG, containing an aqueous solution in the core.

The fate and disposition of intravenously injected liposomes depend on their physical properties, such as size, fluidity, and surface charge. They may persist in tissues for h or days, depending on their composition, and half lives in the blood range from min to several h. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominant site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow, and lymphoid organs.

Alternatively, the invention provides for pharmaceutically-acceptable nanocapsule formulations of the compositions of the present invention. Nanocapsules can generally entrap compounds in a stable and reproducible way (Baszkin et al., 1987; Quintanar-Guerrero et al., 1998; Douglas et al., 1987). To avoid side effects due to intracellular polymeric overloading, such ultrafine particles (sized around 0.1. mu.m) should be designed using polymers able to be degraded in vivo. Biodegradable polyalkyl-cyanoacrylate nanoparticles that meet these requirements are contemplated for use in the present invention. Such particles may be easily made, as described (Couvreur et al., 1980; 1988; zur Muhlen et al., 1998; Zambaux et al. 1998; Pinto-Alphandry et al., 1995 and U.S. Pat. No. 5,145,684, specifically incorporated herein by reference in its entirety).

E. Treatment of Pathophysiological States

1. Definitions

A "pathophysiological state" is defined herein to refer to a disease or health-related condition. "Treatment" and "treating" as used herein refer to administration or application of a therapeutic agent to a subject or performance of a procedure or modality on a subject for the purpose of obtaining a therapeutic benefit of a disease or health-related condition. For example, a therapeutic polypeptide of the present invention can be administered for the purpose of reducing temperature in a patient with high body temperature or reducing symptoms of congestive heart failure in a patient with congestive heart failure.

The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease.

"Prevention" and "preventing" are used according to their ordinary and plain meaning to mean "acting before" or such an act. In the context of a particular disease or health-related condition, those terms refer to administration or application of an agent, drug, or remedy to a subject or performance of a procedure or modality on a subject for the purpose of blocking the onset of a disease or health-related condition.

2. Pathophysiological States to be Treated or Prevented

The polypeptides and polynucleotides of the present invention can be applied in the treatment or prevention of any disease or health-related condition. The disease or health-related condition can be any disease or health-related condition for which administration of the polypeptides or polynucleotides of the present invention are known or suspected to be of value. Examples include, but are not limited to high body temperature, appetite dysfunction, congestive heart failure, stress, anxiety, and undesirably low levels of ACTH secretion.

3. Secondary Treatment

Certain embodiments of the present invention provide for the administration or application of one or more secondary forms of therapies for the treatment or prevention of a pathophysiological state.

The secondary form of therapy may be administration of one or more secondary pharmacological agents that can be applied in the treatment or prevention of a pathophysiological state.

If the secondary therapy is a pharmacological agent, it may be administered prior to, concurrently, or following administration of the polypeptide or polynucleotide of the present invention.

The interval between the polypeptide or polynucleotide of the present invention and the secondary therapy may be any interval as determined by those of ordinary skill in the art. For example, the interval may be minutes to weeks. In embodiments where the agents are separately administered, one would generally ensure that a significant period of time did not expire between the time of each delivery, such that each therapeutic agent would still be able to exert an advantageously combined effect on the subject. For example, the interval between therapeutic agents may be about 12 h to about 24 h of each other and, more preferably, within about 6 hours to about 12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations. In some embodiments, the timing of administration of a secondary therapeutic agent is determined based on the response of the subject to the the polypeptide or polynucleotide of the present invention.

F. Kits and Diagnostics

In various aspects of the invention, a kit is envisioned containing one or more polypeptides or polynucleotides of the present invention. In some embodiments, the present invention contemplates a kit for preparing and/or administering a therapy of the invention. The kit may comprise one or more sealed vials containing any of the pharmaceutical compositions of the present invention. In some embodiments, the kit may also comprise a suitable container means, which is a container that will not react with components of the kit, such as an eppendorf tube, an assay plate, a syringe, a bottle, or a tube. The container may be made from sterilizable materials such as plastic or glass.

The kit may further include an instruction sheet that outlines one or more methods of the invention, and will follow substantially the same procedures as described herein or are known to those of ordinary skill. The instruction information may be in a computer readable media containing machine-readable instructions that, when executed using a computer, cause the display of a real or virtual procedure of delivering a pharmaceutically effective amount of a therapeutic agent.

G. Transgenic Animals

Transgenic animals and cell lines derived from such animals may find use in certain testing experiments. In one embodiment of the invention, transgenic animals are produced which contain a functional transgene encoding a polypeptide of the present invention. Such transgenic animals may be useful in methods for identifying additional therapeutic applications of the claimed polypeptides. Transgenic animals of the present invention also can be used as models for studying indications.

In one embodiment of the invention, a transgene is introduced into a non-human host to produce a transgenic animal expressing a polypeptide of the present invention. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. (1985); which is incorporated herein by reference in its entirety) and in "Manipulating the Mouse Embryo; A Laboratory Manual" (1994); which is incorporated herein by reference in its entirety).

Transgenic animals may be produced by any method known to those of ordinary skill in the art. For example, they can be produced from the fertilized eggs from a number of animals including, but not limited to reptiles, amphibians, birds, mammals, and fish. Within a particular embodiment, transgenic mice are generated which overexpress a polypeptide of the present invention.

H. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Identification of Biologically Active Urocortin 2 Polypeptides

Urocortin 2 precursors were overexpressed in various cell lines, and their function was evaluated. Pancreatic and skin cell lines were infected with mouse urocortin 2 (mUcn 2) lentivirus. The amino acid sequence of mouse urocortin 2 is provided as SEQ ID NO:10. The cells were found to secrete a precursor and a smaller processed zone which contained a urocortin peptide: $R^0$mUcn 2 (SEQ ID NO:11) which was C-terminally amidated. The peptide was synthesized and bioactivity was determined by the stimulation of cAMP accumulation in A7r5 cells, which express CRFR2. The $R^0$mUcn 2 peptide was found to be equipotent to mUcn 2(1-38), with $EC_{50}$s of 0.05 $(0.028-0.1)^2$ nM and 0.07 $(0.03-0.15)^{11}$ nM, respectively. It is possible that $R^0$mUcn 2 could be further processed by aminopeptidases to mUcn 2(1-38). Number of assays are depicted as a superscript.

The corresponding human analog, $R^0$hUcn 2, was synthesized. This peptide was found to be equipotent to hUcn 2(1-38) in the ability to stimulate cAMP accumulation in A7r5 cells, with $EC_{50}$s of 0.027 $(0.023-0.031)^2$ nM and 0.11 $(0.058-0.21)^{11}$ nM, respectively.

A peptide extended with a hydrophilic arginine residue such as $R^0$hUcn 2 is likely more soluble, and therefore, a better pharmaceutical agent, than hUcn 2(1-38). As evidence of increased solubility, QC reverse phase HPLC using a trifluoroacetic acid/acetonitrile solvent system showed the retention time of hUcn 2(1-38) was 16.9 minutes whereas the retention time of $R^0$hUcn 2 was 13.9 minutes, demonstrating significantly increased hydrophilicity for the arginine extended analog. Table 2 provides sequence information of selected Ucn 2 sequences.

TABLE 2

Sequence Information

| Peptide | Sequence Identifier | Sequence |
|---|---|---|
| hUcn 2-OH | SEQ ID NO: 1 | IVLSLDVPIGLLQILLEQARARAAREQATTNARILARV |
| hUcn 2-G-OH | SEQ ID NO: 2 | IVLSLDVPIGLLQILLEQARARAAREQATTNARILARVG |
| hUcn 2-GH-OH | SEQ ID NO: 3 | IVLSLDVPIGLLQILLEQARARAAREQATTNARILARVGH |
| hUcn 2-GHC-OH | SEQ ID NO: 4 | IVLSLDVPIGLLQILLEQARARAAREQATTNARILARVGHC |
| hUcn 2 | SEQ ID NO: 5 | IVLSLDVPIGLLQILLEQARARAAREQATTNARILARV-NH.sub.2 (amidated at the C-terminus) |
| $R^0$-hUcn 2 | SEQ ID NO: 6 | RIVLSLDVPIGLLQILLEQARARAAREQATTNARILARV-NH.sub.2 (amidated at the C-terminus) |
| SRP (HPGSR-hUcn 2) | SEQ ID NO: 7 | HPGSRIVLSLDVPIGLLQILLEQARARAAREQATTNARILARV-NH.sub.2 (amidated at the C-terminus) |
| [$Cys^{1,51}$(Acm)]-hUcn 2(1-51)-OH | SEQ ID NO: 8 | CSPTRHPGSRIVLSLDVPIGLLQILLEQARARAAREQATTNARILARVGHC |
| hUcn 2 prohormone | SEQ ID NO: 9 | IPTFQLRPQNSPQTTPRPAASESPSAAPTWPWAAQSHCSPTRHPGSRIVLSLDVPIGLLQILLEQARARAAREQATTNARILARV-NH$_2$ (amidated at the C-terminus) |
| mUcn2-OH | SEQ ID NO: 21 | VILSLDVPIGLLRILLEQARYKAARNQAATNAQILAHV |
| mUcn 2 | SEQ ID NO: 10 | VILSLDVPIGLLRILLEQARYKAARNQAATNAQILAHV (amidated at the C-terminus) |
| $R^0$-mUcn 2 | SEQ ID NO: 11 | RVILSLDVPIGLLRILLEQARYKAARNQAATNAQILAHV (amidated at the C-terminus) |

TABLE 2-continued

Sequence Information

| Peptide | Sequence Identifier | Sequence |
|---|---|---|
| mUcn 2 prohormone-OH | SEQ ID NO: 22 | RVILSLDVPIGLLRILLEQARYKAARNQAATNAQILAHV |
| mUcn 2 prohormone | SEQ ID NO: 12 | TPIPTFQLLPQNSLETTPSSVTSESSSGTTTGPSASWSNS KASPYLDTRVILSLDVPIGLLRILLEQARYKAARNQAA TNAQILAHV (amidated at the C-terminus) |
| $R^0$-hUcn 2-G-OH | SEQ ID NO: 13 | RIVLSLDVPIGLLQILLEQARARAAREQATTNARILARVG |
| $R^0$-hUcn 2-GH-OH | SEQ ID NO: 14 | RIVLSLDVPIGLLQILLEQARARAAREQATTNARILARVGH |
| $R^0$-hUcn 2-GHC-OH | SEQ ID NO: 15 | RIVLSLDVPIGLLQILLEQARARAAREQATTNARILARVGHC |
| hUcn 2 prohormone-G-OH | SEQ ID NO: 16 | IPTFQLRPQNSPQTTPRPAASESPSAAPTWPWAAQSHC SPTRHPGSRIVLSLDVPIGLLQILLEQARARAAREQATT NARILARVG |
| hUcn 2 prohormone-GH-OH | SEQ ID NO: 17 | IPTFQLRPQNSPQTTPRPAASESPSAAPTWPWAAQSHC SPTRHPGSRIVLSLDVPIGLLQILLEQARARAAREQATT NARILARVGH |
| hUcn 2 prohormone-GHC-OH | SEQ ID NO: 18 | IPTFQLRPQNSPQTTPRPAASESPSAAPTWPWAAQSHC SPTRHPGSRIVLSLDVPIGLLQILLEQARARAAREQATT NARILARVGHC |
| hUcn 2 prohormone-OH | SEQ ID NO: 19 | IPTFQLRPQNSPQTTPRPAASESPSAAPTWPWAAQSHC SPTRHPGSRIVLSLDVPIGLLQILLEQARARAAREQATT NARILARV |

Table 3 shows a comparison of amino acid sequences and bioactivity of selected synthetic human or human Ucn 2 peptide analogues. The EC50s were calculated based on protein determination by immunoassay and chromatographic peak height.

TABLE 3

Bioactivity of Selected Synthetic Human or Mouse Ucn 2 Peptides/Analogues

| Peptide | SEQUENCE IDENTIFIER | cAMP A7r5 (EC$_{50}$, nM) [Number of Assays] |
|---|---|---|
| hUcn 2-OH | SEQ ID NO: 1 | 90.4 (47-172) [3] |
| hUcn 2-G-OH | SEQ ID NO: 2 | 6.3 (3.4-11.5) [2] |
| hUcn 2-GH-OH | SEQ ID NO: 3 | 2.9 (0.93-9.1) [2] |
| hUcn 2-GHC-OH | SEQ ID NO: 4 | 13.9 (11.3-17) [2] |
| hUcn 2 | SEQ ID NO: 5 | 0.11 (0.058-0.21) [11] |
| $R^0$ hUcn 2 | SEQ ID NO: 6 | 0.027 (0.023-0.031) [2] |
| SRP (HPGSR-hUcn 2) | SEQ ID NO: 7 | 0.09 (0.033-0.22) [2] |
| [Cys$^{1,51}$(Acm)]-hUcn 2(1-51)-OH | SEQ ID NO: 8 | 9.5 (3.3-26.8) [3] |
| hUcn 2 prohormone | SEQ ID NO: 9 | 2.3 (1.8-3) [2] |
| mUcn 2 | SEQ ID NO: 10 | 0.07 (0.03-0.15) [11] |
| $R^0$-mUcn 2 | SEQ ID NO: 11 | 0.05 (0.03-0.1) [2] |
| mUcn 2 prohormone | SEQ ID NO: 12 | 0.53 (0.4-0.8) [2] |

All of the methods disclosed and claimed herein can be made and executed without undue experimentation in light of the present disclosure. While the methods of this invention have been described in terms of preferred embodiments, it will be apparent to those of skill in the art that variations may be applied to the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,659,774
U.S. Pat. No. 4,682,195
U.S. Pat. No. 4,683,202
U.S. Pat. No. 4,816,571
U.S. Pat. No. 4,873,191
U.S. Pat. No. 4,879,236
U.S. Pat. No. 4,959,463
U.S. Pat. No. 5,141,813
U.S. Pat. No. 5,145,684
U.S. Pat. No. 5,264,566
U.S. Pat. No. 5,428,148
U.S. Pat. No. 5,552,157
U.S. Pat. No. 5,554,744
U.S. Pat. No. 5,565,213
U.S. Pat. No. 5,567,434
U.S. Pat. No. 5,574,146
U.S. Pat. No. 5,580,579
U.S. Pat. No. 5,602,244
U.S. Pat. No. 5,641,515
U.S. Pat. No. 5,645,897
U.S. Pat. No. 5,705,629
U.S. Pat. No. 5,738,868
U.S. Pat. No. 5,741,516
U.S. Pat. No. 5,792,451
U.S. Pat. No. 5,795,587
U.S. Pat. No. 5,871,986
U.S. Pat. No. 6,214,797
U.S. Pat. No. 6,353,152
U.S. Pat. No. 6,838,274
U.S. Pat. No. 7,141,546
U.S. Pat. No. 7,223,846
U.S. Pat. No. 7,459,427
U.S. Pat. No. 7,488,865
U.S. Pat. No. 7,507,794
U.S. Patent Publn. 20030032587
U.S. Patent Publn. 20050191650
U.S. Patent Publn. 20070042954
U.S. Patent Publn. 20070191592
U.S. Patent Publn. 20080161235
Allen and Choun, *FEBS Lett.*, 223(1):42-46, 1987.
Avis, Remington's Pharmaceutical Sciences, 18th Ed., Gennaro (Ed.), Mack Publishing Co., Pa., 84:1545-1569, 1990.
Baichwal and Sugden, In: *Gene Transfer*, Kucherlapati (Ed.), Plenum Press, NY, 117-148, 1986.
Baszkin et al., *J. Pharm. Pharmacol.*, 39(12):973-977. 1987
Benet et al., In: *Goodman & Gilman's The Pharmacological Basis of Therapeutics*, Hardman et al. (Eds.), McGraw-Hill, NY, Chap. 1, 9th Ed., 1996.
Benvenisty and Neshif, *Proc. Natl. Acad. Sci. USA*, 83(24): 9551-9555, 1986.
Brinster et al., *Proc. Natl. Acad. Sci. USA*, 82(13):4438-4442, 1985.
Chandran et al., *Indian J. Exp. Biol.*, 35(8):801-809., 1997.
Chen and Okayama, *Mol. Cell Biol.*, 7(8):2745-2752, 1987.
Coffin, In: *Virology*, Fields et al. (Eds.), Raven Press, NY, 1437-1500, 1990.
Coupar et al., *Gene*, 68:1-10, 1988.
Couvreur et al., *FEBS Lett.*, 84(2):323-326, 1977.
Couvreur et al., *J. Pharm. Sci.*, 69(2):199-202, 1980.
Couvreur, *Crit. Rev. Ther. Drug Carrier Syst.*, 5(1):1-20, 1988.
Davidson et al., *Biochem. Pharmacol.*, 77(2):141-50, 2009.
Derossi et al., *J. Biol. Chem.*, 269(14):10444-10450, 1994.
Douglas et al., *Crit. Rev. Ther. Drug Carrier Syst.*, 3(3):233-61, 1987.
Dubensky et al., *Proc. Natl. Acad. Sci. USA*, 81:7529-7533, 1984.
Elliott and O'Hare, *Cell*, 88(2):223-233, 1997.
EP 266,032
EPO 0273085
Ettinger et al., *Cancer*, 41:1270, 1978.
Fechheimer et al., *Proc Natl. Acad. Sci. USA*, 84:8463-8467, 1987.
Ferkol et al., *FASEB J.*, 7:1081-1091, 1993.
Fraley et al., *Proc. Natl. Acad. Sci. USA*, 76:3348-3352, 1979.
Freshner, 1992
Friedmann, *Science*, 244:1275-1281, 1989.
Froehler et al., *Nucleic Acids Res.*, 14:5399-5407, 1986.
Gabizon and Papahadjopoulos, *Proc. Natl. Acad. Sci. USA*, 85(18):6949-6953, 1988.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Gomez-Foix et al., *J. Biol. Chem.*, 267:25129-25134, 1992.
Gopal, *Mol. Cell Biol.*, 5:1188-1190, 1985.
Graham and Prevec, *Biotechnology*, 20:363-390, 1992.
Graham and Van Der Eb, *Virology*, 52:456-467, 1973.
Graham et al., *J. Gen. Virl.*, 36(1):59-74, 1977.
Grunhaus and Horwitz, *Seminar in Virology*, 3:237-252, 1992.
Grunhaus and Horwitz, *Seminar in Virology*, 3:237-252, 1992.
Harland and Weintraub, *J. Cell Biol.*, 101(3):1094-1099, 1985.
Harvey, Remington's Pharmaceutical Sciences, 18th Ed., Gennaro Ed.), Mack Publishing Co., Pa., 35:711, 1990.
Hermonat and Muzycska, *Proc. Natl. Acad. Sci. USA*, 81:6466-6470, 1984.
Herz and Gerard, *Proc. Natl. Acad. Sci. USA*, 90:2812-2816, 1993.
Horwich et al. *J. Virol.*, 64:642-650, 1990.
Hsu and Hsueh, *Nat. Med.*, 7605-611, 2001.
Hwang et al., *Crit. Rev. Ther. Drug Carrier Syst.*, 15(3): 243-284, 1998.
Kaneda et al., *Science*, 243:375-378, 1989.
Kato et al, *J. Biol. Chem.*, 266:3361-3364, 1991.
Kemeny et al., *Cancer*, 71:1964, 1993.
Klein et al., *Nature*, 327:70-73, 1987.
Lasic, *Trends Biotechnol.*, 16(7):307-321, 1998.
Lawrence and Latchman, *Mini Rev. Med. Chem.*, 6(10): 1119-26, 2006
Le Gal La Salle et al., *Science*, 259:988-990, 1993.
Levrero et al., *Gene*, 101:195-202, 1991.
Luer and Hatton, In: *The Annals of Pharmacotherapy*, 27:912, 1993.
*Manipulating the Mouse Embryo; A Laboratory Manual*, 2nd Ed., Hogan et al., (Eds.), Cold Spring Harbor Laboratory Press, 1994
Mann et al., *Cell*, 33:153-159, 1983.
Margalit, *Crit. Rev. Ther. Drug Carrier Syst.*, 12(2-3):233-261, 1995.
Mathiowitz et al., *Nature*, 386(6623):410-414, 1997.

Morishita et al., *Proc. Natl. Acad. Sci. USA*, 90:8474, 1993.
Nagahara et al., *Am. J. Physiol.*, 275(4 Pt 1):G740-G748, 1998.
Nagahara et al., *Nat. Med.*, 4(12):1449-1452, 1998.
Nicolas and Rubenstein, In: *Vectors: A survey of molecular cloning vectors and their uses*, Rodriguez and Denhardt, eds., Stoneham: Butterworth, pp. 494-513, 1988.
Nicolau and Sene, *Biochim. Biophys. Acta*, 721:185-190, 1982.
Nicolau et al., *Methods Enzymol.*, 149:157-176, 1987.
Paskind et al., *Virology*, 67:242-248, 1975.
Perales et al., *Proc. Natl. Acad. Sci. USA*, 91:4086-4090, 1994.
Pinto-Alphandary et al., *J. Drug Target*, 3(2):167-169, 1995.
Potter et al., *Proc. Natl. Acad. Sci. USA*, 81:7161-7165, 1984.
Quintanar-Guerrero et al., *Drug Dev. Ind. Pharm.*, 24(12): 1113-28, 1998.
Raddino et al., *G. Ital. Cardiol (Rome)*, 8(4):236-245, 2007
Ragot et al., *Nature*, 361:647-650, 1993.
Remington's Pharmaceutical Sciences, 15$^{th}$ ed., 33:624-652, Mack Publishing Company, Easton, Pa., 1980.
Remington's Pharmaceutical Sciences, 18th Ed. Mack Printing Company, 1289-1329, 1990.
Remington's Pharmaceutical Sciences, 18$^{th}$ Ed., Gennaro (Ed.), MachPublishing Co., Block, Chapter 87:1609-1614, 1990.
Rich et al., *Hum. Gene Ther.*, 4:461-476, 1993.
Ridgeway, In: *Vectors: A Survey of Molecular Cloning Vectors and Their Uses*, Rodriguez et al. (Eds.), Stoneham: Butterworth, 467-492, 1988.
Rippe, et al., *Mol. Cell Biol.*, 10:689-695, 1990.
Rosenfeld et al., *Science*, 252:431-434, 1991.
Rosenfeld, et al., *Cell*, 68:143-155, 1992.
Sambrook et al., In: *Molecular cloning*, Cold Spring Harbor Laboratory Press, Cold Spring Harbor, NY, 2001.
Shaw, *Cancer*, 72(11):3416, 1993.
Stratford-Perricaudet and Perricaudet, In: *Human Gene Transfer*, Eds, Cohen-Haguenauer and Boiron, John Libbey Eurotext, France, 51-61, 1991.
Stratford-Perricaudet et al., *Hum. Gene. Ther.*, 1:241-256, 1990.
Takakura, *Nippon Rinsho.*, 56(3):691-695, 1998.
Temin, In: *Gene Transfer*, Kucherlapati (Ed.), NY, Plenum Press, 149-188, 1986.
Tur-Kaspa et al., *Mol. Cell Biol.*, 6:716-718, 1986.
Wagner et al., *Proc. Natl. Acad. Sci. USA* 87(9):3410-3414, 1990.
Wong et al., *Gene*, 10:87-94, 1980.
Wu and Wu, *Adv. Drug Delivery Rev.*, 12:159-167, 1993.
Wu and Wu, *Biochemistry*, 27: 887-892, 1988.
Wu and Wu, *J. Biol. Chem.*, 262:4429-4432, 1987.
Wu and Wu, *J. Biol. Chem.*, 262:4429-4432, 1987.
Yaida et al., *Regul. Pept.*, 59:193, 1995.
Yang and Russell, *Proc. Natl. Acad. Sci. USA*, 87:4144-4148, 1990.
Yang et al. *Proc. Natl. Acad. Sci. USA*, 87:4144-4148, 1990.
Zambaux et al., *J. Control Release*, 50(1-3):31-40, 1998.
Zelenin et al., *FEBS Lett.*, 287(1-2):118-120, 1991.
Zimm et al., *Cancer Research*, 44:1698, 1984.
zur Muhlen et al., *Eur. J. Pharm. Biopharm.*, 45(2):149-155, 1998.

The invention claimed is:

1. An isolated nucleic acid molecule encoding SEQ ID NO: 6 or SEQ ID NO: 11 linked to a heterologous regulatory element.

2. The nucleic acid molecule of claim 1, wherein said nucleic acid is dispersed in a lipid particle, a liposome, a vesicle, a nanosphere, or a nanoparticle.

3. A kit comprising the nucleic acid molecule of claim 1.

4. The isolated nucleic acid molecule of claim 1, wherein the molecule is in a vector.

5. The isolated nucleic acid molecule of claim 4, wherein the vector is in a host cell.

6. The nucleic acid molecule of claim 4, wherein the vector is a viral vector.

7. The nucleic acid molecule of claim 6, wherein the viral vector is an adenoviral vector, a lentiviral vector, or an adeno-associated viral vector.

8. The nucleic acid molecule of claim 5, wherein the host cell is a bacterial cell, a mammalian cell, a plant cell, a yeast cell or an insect cell.

9. The nucleic acid molecule of claim 8, wherein the yeast cell is *P. pastoris*.

10. The nucleic acid molecule of claim 5, wherein said host cell is a prokaryotic host cell.

11. The nucleic acid molecule of claim 10, wherein the prokaryotic host cell is *E. coli, S. tymphimurium, S. marcescens* or *B. subtilis*.

12. The nucleic acid molecule of claim 5, wherein host cell is a mammalian cell.

13. The nucleic acid molecule of claim 12, wherein the mammalian cell is a human cell.

14. A composition comprising a nucleic acid molecule encoding SEQ ID NO: 6 or SEQ ID NO: 11 linked to a heterologous regulatory sequence, dispersed in a pharmaceutically-acceptable, sterile solution.

15. The composition of claim 14, wherein the composition is an injectable solution or dispersion.

16. The composition of claim 14, further comprising one or more of a coating, a surfactant, an antibacterial/antifungal agent, an isotonic agent, or an agent for delaying absorption.

17. A kit comprising the composition of claim 14.

18. A method of producing a polypeptide as set forth in SEQ ID NO: 6 or SEQ ID NO: 11 comprising transferring a nucleic acid molecule encoding SEQ ID NO: 6 or SEQ ID NO: 11, linked to a heterologous regulatory element, into a cell under conditions that allow expression of the nucleic acid molecule, thereby producing the polypeptide.

19. A method of expressing a polypeptide as set forth in SEQ ID NO: 6 or SEQ ID NO: 11 in a host organism comprising transferring a composition a nucleic acid molecule encoding SEQ ID NO: 6 or SEQ ID NO: 11, linked to a heterologous regulatory element and a pharmaceutically-acceptable, sterile solution into said organism.

* * * * *